US012484928B2

(12) United States Patent
Kobayashi et al.

(10) Patent No.: US 12,484,928 B2
(45) Date of Patent: Dec. 2, 2025

(54) MEDICAL DEVICE

(71) Applicant: TERUMO KABUSHIKI KAISHA, Tokyo (JP)

(72) Inventors: Junichi Kobayashi, Cupertino, CA (US); Yuichi Tada, Santa Clara, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 671 days.

(21) Appl. No.: 17/876,441

(22) Filed: Jul. 28, 2022

(65) Prior Publication Data

US 2022/0361913 A1 Nov. 17, 2022

Related U.S. Application Data

(63) Continuation of application No. PCT/JP2020/014690, filed on Mar. 30, 2020.

(51) Int. Cl.
*A61B 17/3207* (2006.01)
*A61B 17/00* (2006.01)

(52) U.S. Cl.
CPC ................. *A61B 17/320758* (2013.01); *A61B 2017/00022* (2013.01); *A61B 2017/00539* (2013.01)

(58) Field of Classification Search
CPC ........ A61B 17/3207; A61B 17/320783; A61B 17/32075; A61B 17/320725; A61B 2017/00022; A61B 2017/00539; A61B 2017/320775
USPC ................................ 606/159, 169, 170, 171
See application file for complete search history.

(56) References Cited

U.S. PATENT DOCUMENTS 6,001,112 A 12/1999 Taylor
7,666,161 B2 * 2/2010 Nash ....................... A61M 1/80 604/523
7,771,445 B2 * 8/2010 Heitzmann .... A61B 17/320758 606/159
2003/0093098 A1 * 5/2003 Heitzmann .... A61B 17/320758 606/159
2003/0120296 A1 6/2003 Shturman et al.
2007/0282303 A1 * 12/2007 Nash .............. A61B 17/320783 604/510

(Continued)

FOREIGN PATENT DOCUMENTS

WO 2019/188656 A1 10/2019

OTHER PUBLICATIONS

English Translation of International Search Report dated Jun. 30, 2020, mailed in counterpart International Application No. PCT/JP2020/014690, 2 pages.

(Continued)

*Primary Examiner* — Tuan V Nguyen
(74) *Attorney, Agent, or Firm* — Kim & Stewart LLP

(57) ABSTRACT

A medical device for removing an object in a body cavity, includes a rotatable drive shaft having a lumen, a cutter disposed at a distal portion of the drive shaft and by which the object is cut, a drive shaft driving source configured to rotate the drive shaft, a fluid driving source configured to move a fluid from a distal side to a proximal side of the lumen, a switch, and a controller configured to, in response to the switch being turned on, control the fluid driving source to begin moving the fluid, and control the drive shaft driving source to begin rotating the drive shaft a first predetermined period after the switch is turned on.

18 Claims, 5 Drawing Sheets

(56) References Cited

U.S. PATENT DOCUMENTS

| | | | | |
|---|---|---|---|---|
| 2012/0172888 | A1 | 7/2012 | Shugrue et al. | |
| 2015/0105791 | A1* | 4/2015 | Truckai ............ | A61B 17/00234 606/115 |
| 2020/0397465 | A1 | 12/2020 | Nakano et al. | |

OTHER PUBLICATIONS

English Translation of Written Opinion dated Jun. 30, 2020, mailed in counterpart International Application No. PCT/JP2020/014690, 4 pages.

* cited by examiner

MEDICAL DEVICE

CROSS-REFERENCE TO RELATED APPLICATION(S)

This application is a continuation of International Patent Application No. PCT/JP2020/014690 filed Mar. 30, 2020, the entire contents of which are incorporated herein by reference.

BACKGROUND OF THE INVENTION

Field of the Invention

This disclosure relates to a medical device for removing an object in a body cavity and a method performed by a medical device.

Background Art

Examples of a treatment method for a stenosed site caused by a plaque, a thrombus, and the like in a blood vessel include a method for dilating the blood vessel by using a balloon, and a method for causing a mesh-shaped or coil-shaped stent to indwell the blood vessel as a support for the blood vessel. However, it is difficult for these methods to treat a stenosed site that is hardened by calcification or a stenosed site that is formed at a bifurcated portion in the blood vessel. Thus, methods for cutting and removing a stenotic material such as a plaque or a thrombus using a medical device with an atherectomy device have been developed and used.

Examples of a risk of a procedure by such an atherectomy device include peripheral embolization due to debris caused by a plaque or the like cut by the atherectomy device. Ablation or the like using a laser has been provided as a solution to reduce the risk, but an atherectomy device including a mechanical ablation unit is still effective in a lesion associated with heavy calcification.

There exists a medical device using a mechanical cutting method and having a function of taking debris into a lumen of the medical device, but it is difficult to collect a calcified lesion having particularly high hardness.

In the atherectomy device, aspiration is started simultaneously with a start of rotation of a cutting portion. Alternatively, when the cutting portion starts to rotate, a negative pressure for drawing debris into the lumen is generated. Therefore, there is a high risk that the negative pressure for drawing debris into the lumen is not sufficient immediately after the start of the rotation of the cutting portion, and the debris cannot be sufficiently collected immediately after the start of the rotation.

For example, there exists a conventional medical device having a mechanical mechanism in which, when an operation switch is operated, a lumen is first opened, and then a switch of a motor that rotates a cutting portion is turned on.

In such a medical device, when the operation switch is operated, aspiration in the lumen is first started, and then the switch of the motor is turned on to start cutting by the cutting portion. However, since the switch of the motor is operated by the mechanical mechanism, a delay time from the start of the aspiration in the lumen to a start of rotation of the motor cannot be adjusted. Therefore, a sufficient delay time may not be obtained. In addition, the functionality of the medical device depends on rigidity of a tube, and a tube having the lumen may be crushed.

SUMMARY OF THE INVENTION

In one embodiment, a medical device for removing an object in a body cavity includes:

- a rotatable drive shaft having a lumen;
- a cutter disposed at a distal portion of the drive shaft and by which the object is cut;
- a drive shaft driving source configured to rotate the drive shaft;
- a fluid driving source configured to move a fluid from a distal side to a proximal side of the lumen;
- a switch; and
- a controller configured to:
  - in response to the switch being turned on, control the fluid driving source to begin moving the fluid, and
  - control the drive shaft driving source to begin rotating the drive shaft a first predetermined period after the switch is turned on.

In the medical device configured as described above, the driving of the fluid driving source is started first, and the driving of the drive shaft driving source is started with a delay, and thus the cutting by the cutter is started after a sufficient negative pressure is generated at a distal portion of the lumen. A delay time from a start of aspiration in the lumen to a start of rotation of the cutting portion can be freely set and stored in the controller, and the start of the driving of the drive shaft driving source can be reliably delayed regardless of a state of the first switch.

DESCRIPTION OF EMBODIMENTS

Figure 1:
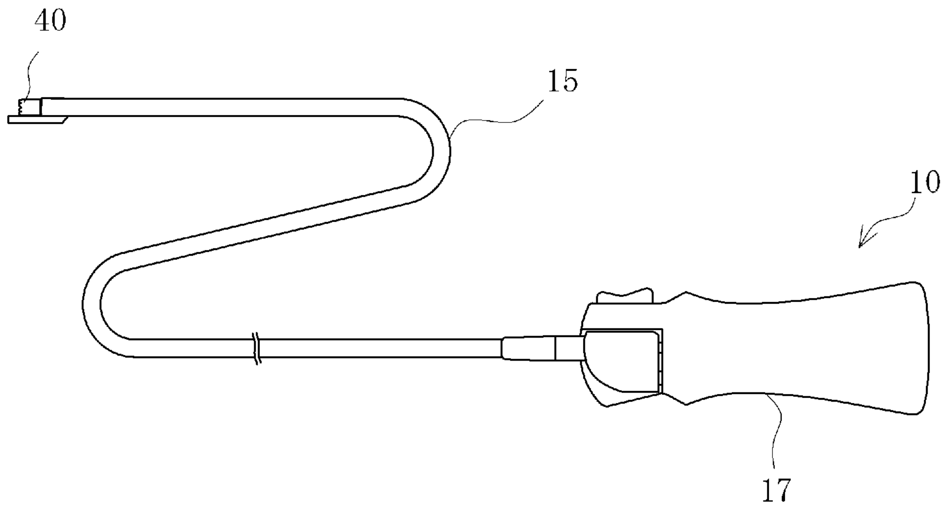
FIG. 1 is an overall front view showing a medical device.

Hereinafter, embodiments according to this disclosure will be described with reference to the drawings. It is noted that dimensional ratios in the drawings are exaggerated for convenience of description and may differ from actual ratios. In the present specification, a side of a medical device 10 to be inserted into a body cavity is referred to as a "distal end" or a "distal side", and a side to be operated by an operator is referred to as a "proximal end" or a "proximal side".

The medical device 10 according to an embodiment is inserted into a blood vessel in an acute lower limb ischemia or a deep vein thrombosis, and is used for a procedure for destroying and removing a thrombus, a plaque, an atheroma, a calcified lesion, and the like. It is noted that an object to be removed is not necessarily limited to the thrombus, the plaque, the atheroma, and the calcified lesion, and any object that may be present in a body lumen or a body cavity can be removed by the medical device 10.

Figure 2:
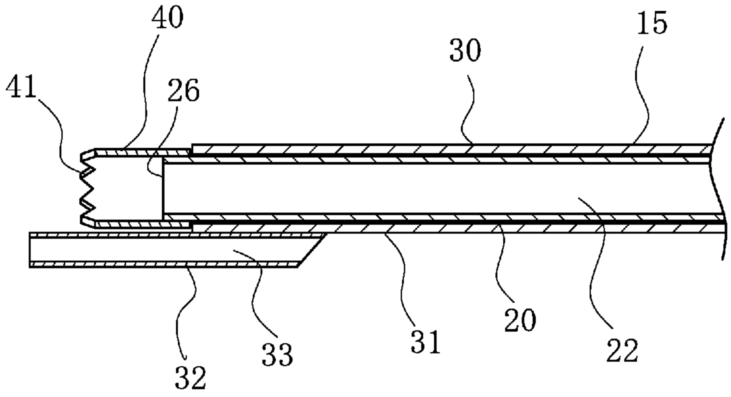
FIG. 2 is an enlarged cross-sectional view showing a distal portion of a medical device.

As shown in FIGS. 1 and 2, the medical device 10 includes a shaft portion 15 including a long drive shaft 20 that is rotationally driven, and an outer tube 30 that accommodates the drive shaft 20. A handle portion 17 is provided at a proximal portion of the shaft portion 15. A cutting portion 40 that cuts an object such as a thrombus is provided at a distal portion of the drive shaft 20.

The drive shaft 20 transmits a rotational force to the cutting portion 40. A lumen 22 for conveying the cut object to the proximal side is formed in the drive shaft 20. The drive shaft 20 penetrates the outer tube 30, and the cutting portion 40 is fixed to the distal portion thereof. The drive shaft 20 includes, at the distal end thereof, an inlet portion 26 into which debris (e.g., cut thrombus or the like), that is, an object to be aspirated, enters.

The drive shaft 20 is flexible and capable of transmitting a rotational power applied from the proximal side to the distal side. The drive shaft 20 may be formed of one member as a whole, or may be formed of a plurality of members. The drive shaft 20 may have a spiral slit or groove formed by laser processing or the like in order to adjust rigidity along the rotational axis. In addition, the distal portion and a proximal portion of the drive shaft 20 may be formed of different members. For example, an inner diameter of the drive shaft 20 is about 0.7 mm to 1.2 mm. A length of the drive shaft 20 is about 1300 mm to 1700 mm. A rotational speed of the drive shaft 20 is 3,000 rpm to 20,000 rpm, preferably 6,000 rpm to 150,000 rpm.

As a constituent material for the drive shaft 20, for example, stainless steel, a shape memory alloy such as a nickel-titanium alloy, an alloy made of silver, copper, zinc, and the like (e.g., silver brazing filler metal), an alloy made of gold, tin, and the like (e.g., solder component), a cemented carbide such as tungsten carbide, polyolefins such as polyethylene and polypropylene, polyamides, polyesters such as polyethylene terephthalate, fluoropolymers such as an ethylene tetrafluoroethylene copolymer (ETFE), polyether ether ketone (PEEK), and polyimides can be preferably used. In addition, the drive shaft 20 may be made of a plurality of materials, and a reinforcing member such as a wire rod may be embedded therein.

The outer tube 30 includes an outer tube main body 31 that rotatably accommodates the drive shaft 20, and a distal tube 32 that is fixed to a side surface of a distal portion of the outer tube main body 31.

The distal portion of the outer tube main body 31 is located on a proximal side of the cutting portion 40. By rotating the outer tube main body 31, the cutting portion 40 can be directed to an object to be removed. In addition, the outer tube main body 31 may include a curved portion bent at a predetermined angle at the distal portion thereof. The curved portion is rotated by the outer tube main body 31, so that the cutting portion 40 can easily contact an object to be removed.

The distal tube 32 is fixed to an outer peripheral surface of the distal portion of the outer tube main body 31. The distal tube 32 has a guide wire lumen 33 into which a guide wire can be inserted. Therefore, the medical device 10 is a rapid exchange type device in which the guide wire lumen 33 is formed only at a distal portion thereof.

Constituent materials for the outer tube main body 31 and the distal tube 32 are not particularly limited, and for example, stainless steel, a shape memory alloy such as a nickel-titanium alloy, an alloy made of titanium, silver, copper, zinc, and the like (e.g., silver brazing filler metal), an alloy made of gold, tin, and the like (e.g., solder component), a cemented carbide such as tungsten carbide, polyolefins such as polyethylene and polypropylene, polyamides, polyesters such as polyethylene terephthalate, or various elastomers, fluoropolymers such as ETFE, PEEK, polyimides, and polyacetal can be preferably used. In addition, the outer tube main body 31 may be made of a plurality of materials, and a reinforcing member such as a wire rod may be embedded therein.

The cutting portion 40 is a cutter that cuts and removes an object such as a thrombus, a plaque, or a calcified lesion. Therefore, the "cut" means applying a force to such an object in contact to make the object smaller. A method for applying the force in the cutting and a shape or a form of the object after the cutting are not limited. The cutting portion 40 has enough strength to cut the above-described object. The cutting portion 40 is fixed to the distal portion of the drive shaft 20. The cutting portion 40 is a cylinder that protrudes toward the distal side with respect to the drive shaft 20. A sharp blade 41 is disposed at the distal end of the cutting portion 40. It is noted that a shape of the blade 41 is not particularly limited. The cutting portion 40 may have a large number of minute abrasive grains instead of the blade 41.

A constituent material for the cutting portion 40 preferably has sufficient strength to cut a thrombus, and for example, stainless steel, titanium, diamond, ceramics, a shape memory alloy such as a nickel-titanium alloy, a cemented carbide such as tungsten carbide, an alloy made of silver, copper, zinc, and the like (e.g., silver brazing filler metal), and high speed steel can be preferably used. The constituent material for the cutting portion 40 may be a resin such as engineering plastics such as polyether ether ketone (PEEK) and polyacetal.

Figure 3:
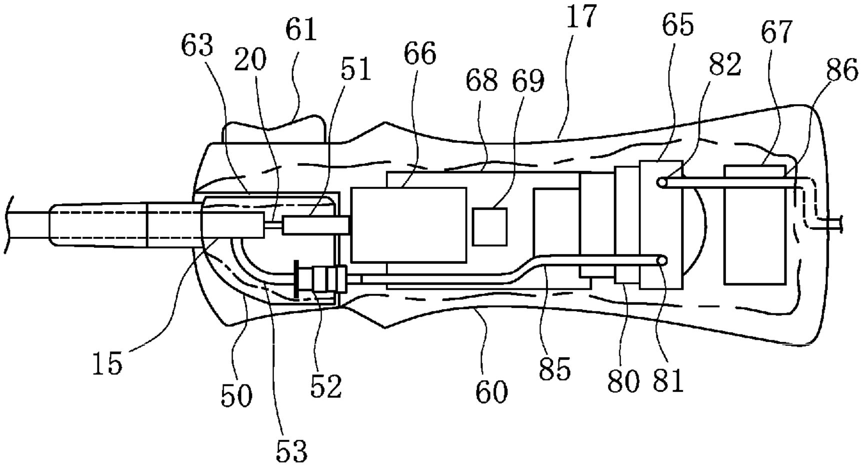
FIG. 3 is an enlarged front view showing an internal structure of a handle portion of a medical device.

The handle portion 17 will be described. As shown in FIG. 3, the handle portion 17 includes a housing 60, and an operation switch 61 for an operator to perform operation is provided on a distal side of the housing 60. A drive shaft driving source 66 such as a motor, a fluid driving source 65 such as a pump, and a power supply portion 67, which is a battery, are accommodated inside the housing 60. The drive shaft driving source 66 rotationally drives the drive shaft 20. The fluid driving source 65 moves a fluid from a distal side to a proximal side of the lumen 22. The power supply portion 67 is connected to the drive shaft driving source 66 and the fluid driving source 65, and supplies a power to them. In addition, a control board 68 including a controller 69 is disposed inside the handle portion 17.

The housing 60 includes a hollow accommodation portion 63 on the distal side thereof. A connector 50 of the shaft portion 15 is provided at the proximal portion thereof and is accommodated in the accommodation portion 63. The connector 50 of the shaft portion 15 includes a rotation connection portion 51 and a fluid connection portion 52 therein. Therefore, the rotation connection portion 51 and the fluid connection portion 52 are integrated.

The shaft portion 15 is branched inside the connector 50. The drive shaft 20 is interlocked with the rotation connection portion 51 of the shaft portion 15 whose central axis is coaxial with the drive shaft 20. The lumen 22 is drawn out toward a branch tube 53 side branched from the shaft portion 15, and the fluid connection portion 52 is provided at a distal portion of the branch tube 53.

The fluid connection portion 52 is connected to the fluid driving source 65. A pump main body 80 of the fluid driving source 65 has an injection port 81 and a discharge port 82. An injection tube 85 extending from a fluid connection portion 72 is connected to the injection port 81. A discharge tube 86 is connected to the discharge port 82. The discharge tube 86 is drawn out to an outside of the housing 60. A part or all of a portion of the discharge tube 86 drawn out to the outside of the housing 60 is transparent or translucent. Accordingly, the operator can visually recognize an inside of the discharge tube 86. The discharge tube 86 is connected to a collection bag (not shown) outside the handle portion 17.

Figure 4:
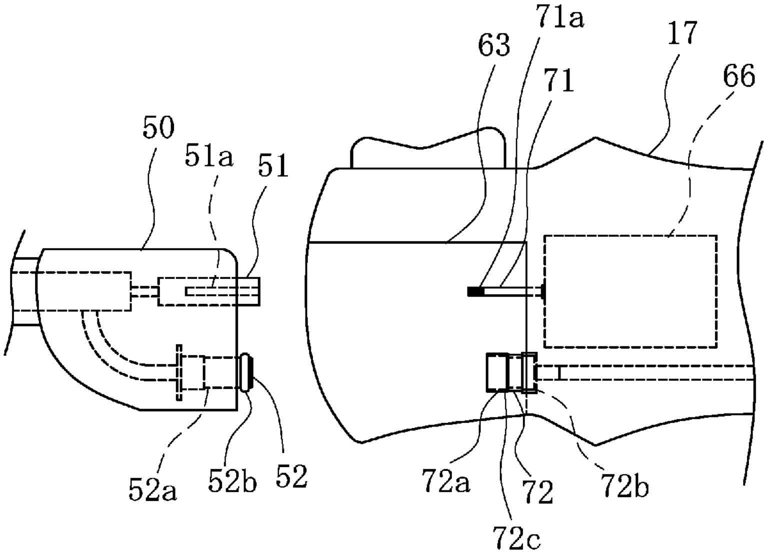
FIG. 4 is an exploded enlarged front view of a handle portion and a connection portion of a shaft portion.

As shown in FIG. 4, the rotation connection portion of the shaft portion 15 includes a shaft insertion portion 51*a* that is open to the proximal side. The drive shaft driving source 66 of the handle portion 17 includes a rotation connection portion 71 protruding into the accommodation portion 63. The rotation connection portion 71 rotates along a rotation axis of the drive shaft driving source 66. The rotation connection portion 71 of the handle portion 17 includes, at a distal portion thereof, a gear portion 71*a* that is fitted to the rotation connection portion 51 of the shaft portion 15. The rotation connection portion 71 of the handle portion 17 is fixed to the housing 60 via the drive shaft driving source 66. When the rotation connection portion 71 of the handle portion 17 is inserted into the shaft insertion portion 51*a* of the rotation connection portion 51 of the shaft portion 15, the gear portion 71*a* is fitted into the shaft insertion portion 51*a*, and thus the rotation connection portion 71 and the rotation connection portion 51 are connected to each other. The rotation connection portion 51 of the shaft portion 15 and the rotation connection portion 71 of the handle portion 17 are fixed so as not to be movable relative to each other in a radial direction and a circumferential direction, but are not fixed in an axial direction. That is, these portions are connected in a state of not being locked to each other.

The fluid connection portion 52 of the shaft portion 15 includes a cylindrical insertion portion 52*a*, and an O-ring 52*b* is attached to a distal portion thereof. The handle portion 17 includes a fluid connection portion 72 which is connected to the fluid connection portion 52 of the shaft portion 15. The fluid connection portion 72 of the handle portion 17 is fixed to the housing 60. The fluid connection portion 72 of the handle portion 17 includes a connector portion 72*a* that accommodates the insertion portion 52*a* of the fluid connection portion 52 of the shaft portion 15. The connector portion 72*a* includes a latch portion 72*b* that latches the fluid connection portion 52 of the shaft portion 15. An inner surface of the connector portion 72*a* has a slightly small diameter on a distal side of the latch portion 72*b*, and the O-ring 52*b* of the insertion portion 52*a* climbs over the small diameter portion and is elastically latched to the latch portion 72*b*. Accordingly, the fluid connection portion 52 of the shaft portion 15 is locked and connected to the fluid connection portion 72 of the handle portion 17.

A connection structure between the rotation connection portion 51 of the shaft portion 15 and the rotation connection portion 71 of the handle portion 17 is different from a connection structure between the fluid connection portion 52 of the shaft portion 15 and the fluid connection portion 72 of the handle portion 17. In addition, the rotation connection portion 51 of the shaft portion 15 and the rotation connection portion 71 of the handle portion 17 are connected in a state of not being locked to each other, and the fluid connection portion 52 of the shaft portion 15 and the fluid connection portion 72 of the handle portion 17 are locked and connected to each other. Therefore, when a lock on an aspiration side is released, connection on a rotation side is also easily released. Accordingly, even when aspiration cannot be performed during a procedure, rotation can be immediately stopped so as not to increase the number of the cut objects in the blood vessel.

The connector portion 72*a* is made of a resin material, and axial front and rear portions of the latch portion 72*b* are a deformable portion 72*c* that is elastically deformable in a radial direction. Therefore, when the operator presses, in the radial direction, the deformable portion 72*c* with a finger so as to deform the deformable portion 72*c*, the deformable portion 72*c* is elastically deformed, and a latch state of the insertion portion 52*a* with respect to the latch portion 72*b* is released accordingly. Therefore, the fluid connection portion 52 of the shaft portion 15 can be easily removed from the connector portion 72*a*. On the other hand, if the operator does not intentionally deform the deformable portion 72*c*, the latch state of the insertion portion 52*a* with respect to the latch portion 72*b* is maintained, and thus it is possible to prevent the fluid connection portion 52 of the shaft portion 15 from being unexpectedly detached from the fluid connection portion 72 of the handle portion 17.

Since both the rotation connection portion 71 of the handle portion 17 and the fluid connection portion 72 of the handle portion 17 are fixed to the housing 60 of the handle portion 17, the rotation connection portion 71 and the fluid connection portion 72 are integrated with each other. As described above, the rotation connection portion 51 of the shaft portion 15 and the fluid connection portion 52 of the shaft portion 15 are also integrated. Therefore, by accommodating the connector 50 of the shaft portion 15 in the accommodation portion 63 of the handle portion 17, the rotation connection portion 51 of the shaft portion 15 can be connected to the rotation connection portion 71 of the handle portion 17, and the fluid connection portion 52 of the shaft portion 15 can be connected to the fluid connection portion 72 of the handle portion 17.

Figure 5:
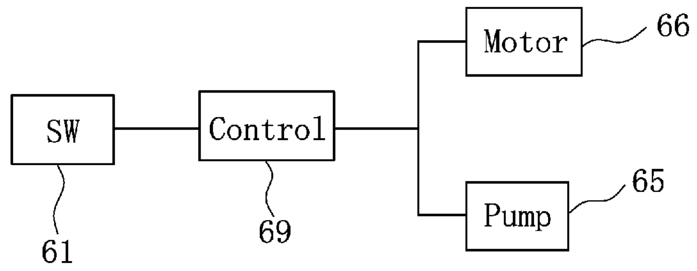
FIG. 5 is a hardware block diagram of a medical device.

Control of the drive shaft driving source 66 and the fluid driving source 65 will be described. As shown in FIG. 5, the first switch 61 is connected to the controller 69. In addition, the controller 69 is connected to and controls the drive shaft driving source 66 and the fluid driving source 65. The first switch 61 outputs a start signal to the controller 69 when the first switch 61 is switched from an off state to an on state by an operation of the operator. In addition, the first switch 61 outputs a stop signal to the controller 69 when the first switch 61 is switched from the off state to the on state by the operation of the operator.

Figure 6:
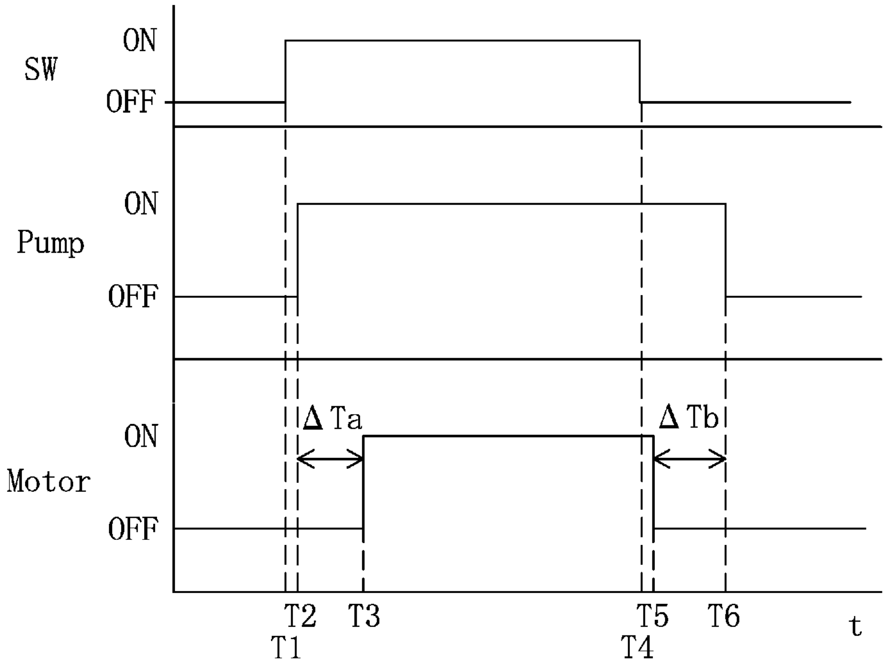
FIG. 6 is an operation time chart of a switch, a pump, and a motor of a medical device.

As shown in FIG. 6, when the first switch 61 outputs the start signal at a time T1, the controller 69 to which the start signal is input starts to drive the fluid driving source 65 at a time T2. The controller 69 starts to drive the drive shaft driving source 66 at a time T3 at which a first predetermined period ΔTa elapses from the time T2. Therefore, the driving of the drive shaft driving source 66 is started with a delay of the first predetermined period ΔTa from the start of the driving of the fluid driving source 65. When the driving of the drive shaft driving source 66 is started, a negative pressure state of the lumen 22 is propagated from a proximal side to a distal side of the shaft portion 20. While the first predetermined period ΔTa elapses from the time T2, the lumen 22 is in the negative pressure state up to a distal portion thereof, and blood is aspirated at a position of the cutting portion 40. Since the drive shaft driving source 66 starts to be driven and the cutting portion 40 starts to rotate in a state in which the aspiration is started at the position of the cutting portion 40 as described above, the debris cut by the cutting portion 40 can be reliably taken into the lumen 22.

The first predetermined period ΔTa can be set in a range of 0.1 seconds to 20 seconds. In addition, the first predetermined period ΔTa can be preferably set in a range of 0.5 seconds to 5 seconds. In addition, the first predetermined period ΔTa is not limited thereto, and may be freely set according to a condition such as the inner diameter and the length of the drive shaft 20 described above.

When the first switch 61 outputs the stop signal at a time T4 during the driving of the drive shaft driving source 66 and the fluid driving source 65, the controller 69 to which the stop signal is input stops the driving of the drive shaft driving source 66 at a time T5. The controller 69 stops the driving of the fluid driving source 65 at a time T6 at which a second predetermined period ΔTb elapses from the time T5. Accordingly, even after the drive shaft driving source 66 is stopped and the cutting by the cutting portion 40 is stopped, the aspiration of the blood is continued for the second predetermined period ΔTb, so that the debris generated by the cutting of the cutting portion 40 can be reliably collected.

The second predetermined period ΔTb can be set in a range of 0.2 seconds to 30 seconds. In addition, the second predetermined period ΔTb can be preferably set in a range of 0.5 seconds to 5 seconds. In addition, the second predetermined period ΔTb is not limited thereto, and may be freely set according to a condition such as the inner diameter and the length of the drive shaft 20 described above.

The second predetermined period ΔTb may be set to 0. In such a case, the drive shaft driving source 66 is stopped simultaneously with the fluid driving source 65. Even if the fluid driving source 65 is stopped simultaneously with the drive shaft driving source 66, the negative pressure state in the lumen 22 at the distal portion of the shaft portion 20 continues for a while. Therefore, the debris can be collected even after the cutting portion 40 is stopped.

By setting the second predetermined period ΔTb to be longer than the first predetermined period ΔTa, the debris remaining in the lumen 22 can be collected more reliably. The first predetermined period ΔTa may be set to be longer than the second predetermined period ΔTb. As described above, even if the fluid driving source 65 is stopped, the negative pressure remains in the lumen 22 for a while, and thus even if the second predetermined period ΔTb is shorter than the first predetermined period ΔTa, the debris may be collected.

Figure 7:
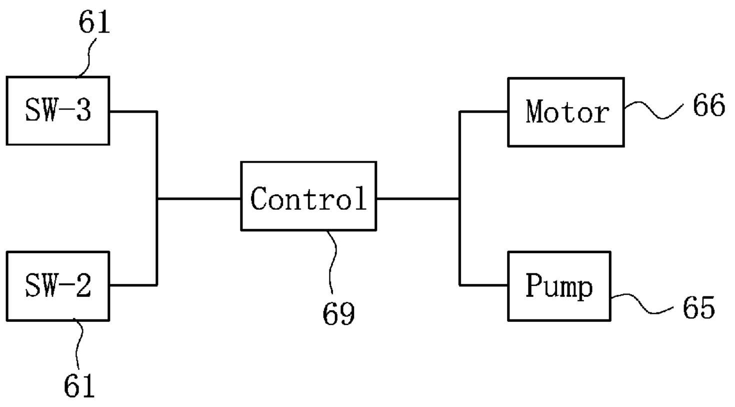
FIG. 7 is a hardware block diagram of a medical device.

As shown in FIG. 7, in one embodiment, the first switch 61 may include a third switch SW-3 for operating the fluid driving source 65 and a second switch SW-2 for operating the drive shaft driving source 66. In one embodiment, the switches SW-2 and SW-3 have the same structure as the switch 61 disposed along the outer surface of the handle portion 17 as shown in FIGS. 1 and 3. The third switch SW-3 and the second switch SW-2 are both connected to the controller 69. The third switch SW-3 can output a fluid start signal for starting the driving of the fluid driving source 65 when the third switch SW-3 is switched from an off state to an on state by the operation of the operator. In addition, the third switch SW-3 can output a fluid stop signal for stopping the driving of the fluid driving source 65 when the third switch SW-3 is switched from the on state to the off state by the operation of the operator. The second switch SW-2 can output a rotation start signal for starting the driving of the drive shaft driving source 66 when the second switch SW-2 is switched from an off state to an on state by the operation of the operator. In addition, the second switch SW-2 can output a rotation stop signal for stopping the driving of the drive shaft driving source 66 when the second switch SW-2 is switched from the on state to the off state by the operation of the operator.

Figure 8:
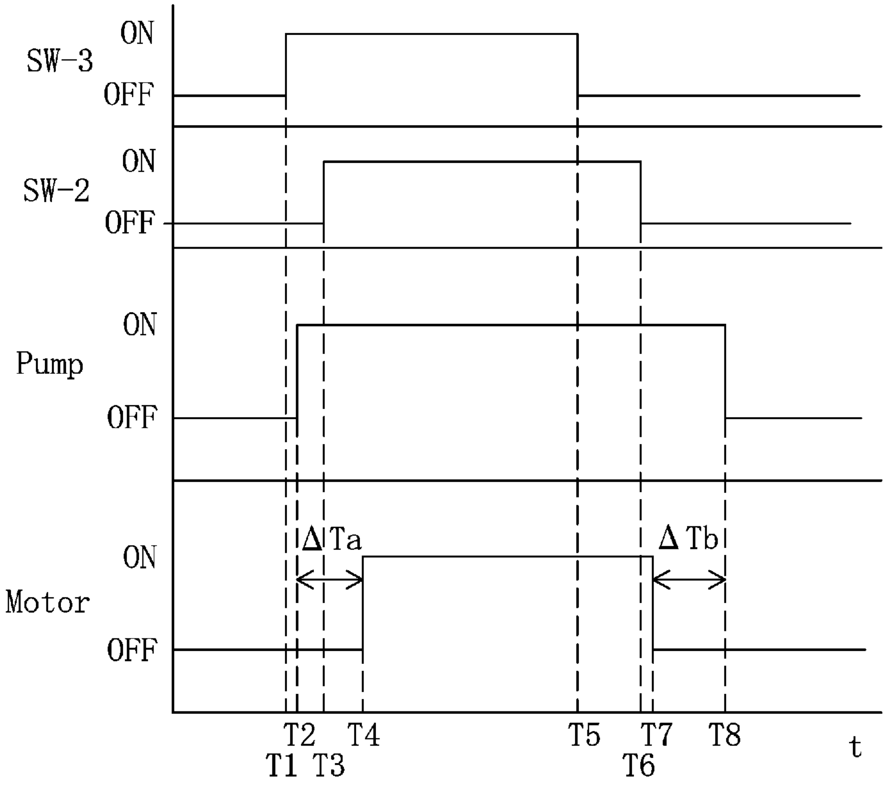
FIG. 8 is an operation time chart of a medical device in a first mode.

As shown in FIG. 8, when the third switch SW-3 outputs the fluid start signal at the time T1, the controller 69 to which the fluid start signal is input starts to drive the fluid driving source 65 at the time T2. Even if the operator operates the second switch SW-2 to output the rotation start signal before the driving of the fluid driving source 65 is started or before the first predetermined period ΔTa elapses from the start of the driving of the fluid driving source 65, the controller 69 does not immediately start to drive the drive shaft driving source 66. When the second switch SW-2 outputs the rotation start signal at the time T3, the controller 69 to which the rotation start signal is input starts to drive the drive shaft driving source 66 at the time T4 at which the first predetermined period ΔTa elapses from the start of the driving of the fluid driving source 65. Accordingly, the fluid driving source 65 can be driven earlier than the drive shaft driving source 66 by the first predetermined period ΔTa.

The time T3 at which the second switch SW-2 is operated is after the driving of the fluid driving source 65 is started, but the same operation is performed even the time T3 is before the driving of the fluid driving source 65 is started. In addition, when the second switch SW-2 is operated after the first predetermined period ΔTa elapses from the start of the driving of the fluid driving source 65, the controller 69 starts to drive the drive shaft driving source 66 at that timing.

Even if the operator operates the third switch SW-3 to output the fluid stop signal during the driving of the drive shaft driving source 66 and the fluid driving source 65, the controller 69 does not immediately stop the driving of the fluid driving source 65. When the second switch SW-2 outputs the rotation stop signal at the time T6 after the third switch SW-3 outputs the fluid stop signal at the time T5, the controller 69 stops the driving of the drive shaft driving source 66 at a time T7, and stops the driving of the fluid driving source 65 at a time T8 at which the second predetermined period ΔTb elapses from the time T7. Accordingly, the fluid driving source 65 can be stopped with a delay of the second predetermined period ΔTb from the stop of the drive shaft driving source 66.

The time T5 at which the third switch SW-3 is operated is before the driving of the drive shaft driving source 66 is stopped, but the same operation is performed even the time T5 is before the second predetermined period ΔTb elapses from the stop of the driving of the drive shaft driving source 66. When the third switch SW-3 is operated after the second predetermined period ΔTb elapses from the stop of the drive shaft driving source 66, the controller 69 stops the driving of the fluid driving source 65 at that timing.

In addition, the controller 69 may perform control such that, when the fluid stop signal is input from the third switch SW-3 or the rotation stop signal is input from the second switch SW-2 during the driving of the drive shaft driving source 66 and the fluid driving source 65, the driving of the drive shaft driving source 66 is stopped at that timing, and after the second predetermined period ΔTb elapses from the stop of the driving of the drive shaft driving source 66, the driving of the fluid driving source 65 is stopped.

Figure 9:
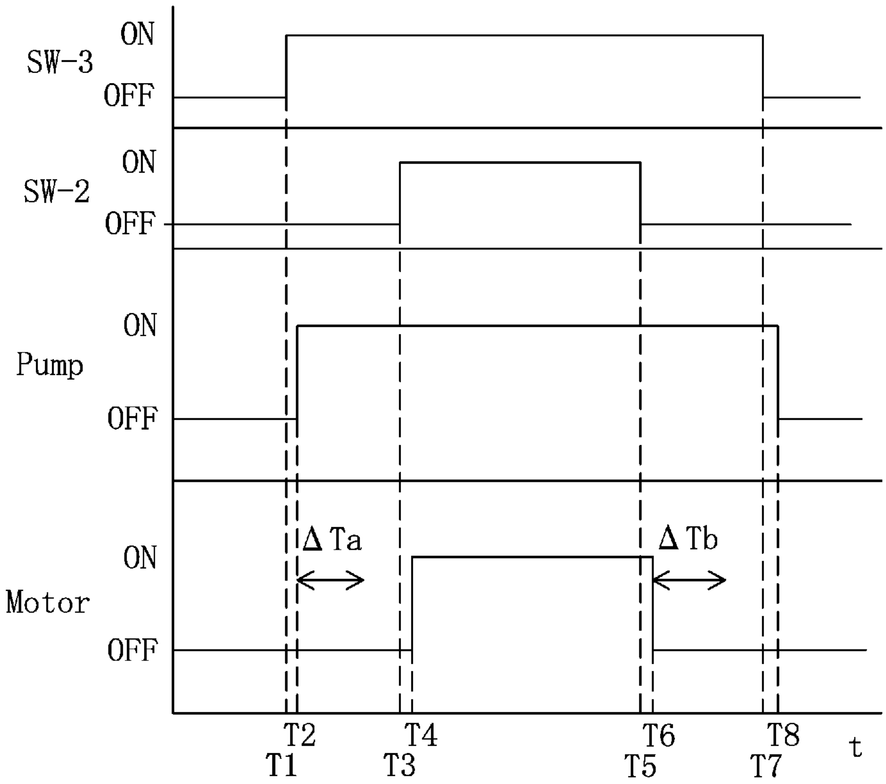
FIG. 9 is an operation time chart of a medical device in a second mode.

The controller 69 can also control the driving and the stopping of the drive shaft driving source 66 and the fluid driving source 65 as follows. As shown in FIG. 9, when the third switch SW-3 outputs the fluid start signal at the time T1, the controller 69 to which the fluid start signal is input starts to drive the fluid driving source 65 at the time T2. Even if the operator operates the second switch SW-2 to output the rotation start signal before the driving of the fluid driving source 65 is started or before the first predetermined period ΔTa elapses from the start of the driving of the fluid driving source 65, the controller 69 ignores the rotation start signal and does not start to drive the drive shaft driving source 66. When the first predetermined period ΔTa elapses from the time T2, the controller 69 enters a state in which the driving of the drive shaft driving source 66 can be started. When the operator operates the second switch SW-2 at the time T3 after the first predetermined period ΔTa elapses from the time T2 and the rotation start signal is input to the controller 69, the controller 69 starts to drive the drive shaft driving source 66 at the time T4. Accordingly, the fluid driving source 65 can be driven earlier than the drive shaft driving source 66 by at least the first predetermined period ΔTa.

Even if the operator operates the third switch SW-3 to output the fluid stop signal during the driving of the drive shaft driving source 66 and the fluid driving source 65 or before the second predetermined period ΔTb elapses from the stop of the driving of the drive shaft driving source 66, the controller 69 ignores the fluid stop signal and does not stop the driving of the fluid driving source 65. When the second switch SW-2 outputs the rotation stop signal at the time T5, the controller 69 stops the driving of the drive shaft driving source 66 at the time T6. When the second predetermined period ΔTb elapses from the time T6, the controller 69 enters a state in which the driving of the fluid driving source 65 can be stopped. When the operator operates the third switch SW-3 at the time T7 after the second predetermined period ΔTb elapses from the time T6 and the fluid stop signal is input to the controller 69, the controller 69 stops the driving of the fluid driving source 65 at the time T8. Accordingly, the driving of the fluid driving source 65 can be stopped with a delay of at least the second predetermined period ΔTb from the stop of the drive shaft driving source 66.

In addition, when the rotation start signal is input again during the second predetermined period ΔTb, the controller 69 ignores the limitation of the driving of the drive shaft driving source 66 and starts the driving thereof until the first predetermined period ΔTa elapses from the start of the driving of the fluid driving source 65 or until a flow rate value of the lumen 22 or the vicinity thereof reaches a set value from the start of the driving of the fluid driving source 65.

It is noted that even when the third switch SW-3 and the second switch SW-2 are separately provided, the second predetermined period ΔTb may be set to 0.

As described above, the medical device 10 according to the above-described embodiments includes: the long shaft portion 20 that includes the drive shaft 20 and the lumen 22; the cutting portion 40 that is disposed at the distal portion of the shaft portion 20 and cuts an object; the drive shaft driving source 66 that rotates the drive shaft 20; the fluid driving source 65 that moves the fluid from the distal side to the proximal side of the lumen 22; the controller 69 that controls the drive shaft driving source 66 and the fluid driving source 65; and the first switch 61 that is connected to the controller 69 and outputs the start signal, in which the controller 69 starts to drive the fluid driving source 65 when the start signal is input from the first switch 61, and limits the driving of the drive shaft driving source 66 until the first predetermined period ΔTa elapses from the start of the driving of the fluid driving source 65 or until the flow rate value of the lumen 22 or the vicinity thereof reaches the set value from the start of the driving of the fluid driving source 65. In the medical device 10 configured as described above, the driving of the fluid driving source 65 is started first, and the driving of the drive shaft driving source 66 is started with a delay, and thus the cutting by the cutting portion 40 is started after a sufficient negative pressure is generated at the distal portion of the lumen 22. The delay time from the start of the aspiration in the lumen 22 to the start of the rotation of the cutting portion 40 can be freely set in the controller 69, and the start of the driving of the drive shaft driving source 66 can be reliably delayed regardless of a mode of the first switch 61.

In addition, in the medical device 10, the controller 69 may start to drive the drive shaft driving source 66 after the first predetermined period ΔTa elapses from the start of the driving of the fluid driving source 65. Accordingly, the driving of the drive shaft driving source 66 can be automatically started with the delay of the first predetermined period ΔTa from the start of the driving of the fluid driving source 65.

Further, in the medical device 10, the first switch 61 may output the stop signal, and the controller 69 may stop the driving of the drive shaft driving source 66 when the stop signal is input from the first switch 61 during the driving of the drive shaft driving source 66 and the fluid driving source 65, and may stop the driving of the fluid driving source 65 after the second predetermined period ΔTb elapses from the stop of the driving of the drive shaft driving source 66. Accordingly, the drive shaft driving source 66 is stopped first, and the fluid driving source 65 is stopped with a delay, and thus the debris generated by the cutting of the cutting portion 40 can be reliably collected.

In addition, in the medical device 10, the first switch 61 may include the second switch SW-2 that outputs the rotation start signal for the drive shaft driving source 66 and the third switch SW-3 that outputs the fluid start signal for the fluid driving source 65, in which the controller 69 may not drive the drive shaft driving source 66 even when the rotation start signal is input from the second switch SW-2 before the driving of the fluid driving source 65 is started or until the first predetermined period ΔTa elapses from the start of the driving of the fluid driving source 65, and may drive the drive shaft driving source 66 when the rotation start signal is input from the second switch SW-2 after the first predetermined period ΔTa elapses from the start of the driving of the fluid driving source 65 after the fluid start signal is input from the third switch 65. Accordingly, the driving of the drive shaft driving source 66 can be started with the delay of the first predetermined period ΔTa or more from the start of the driving of the fluid driving source 65.

In addition, in the medical device 10, the first switch 61 may include the second switch SW-2 that outputs the rotation start signal for the drive shaft driving source 66 and the third switch SW-3 that outputs the fluid start signal for the fluid driving source 65, in which when the rotation start signal is input from the second switch SW-2 before the driving of the fluid driving source 65 is started or until the first predetermined period ΔTa elapses from the start of the driving of the fluid driving source 65, the controller 69 may drive the drive shaft driving source 66 after the first predetermined period ΔTa elapses from the start of the driving of the fluid driving source 65 after the fluid start signal is input from the third switch SW-3. Accordingly, the driving of the drive shaft driving source 66 can be automatically started with the delay of the first predetermined period ΔTa from the start of the driving of the fluid driving source 65.

In addition, in the medical device 10, the second switch SW-2 may output the rotation stop signal for the drive shaft driving source 66, the third switch SW-3 may output the fluid stop signal for the fluid driving source 65, and when the fluid stop signal is input from the third switch SW-3 during the driving of the drive shaft driving source 66 and the fluid driving source 65, or until the second predetermined period ΔTb elapses from the stop of the driving of the drive shaft driving source 66, the controller 69 may stop the driving of the fluid driving source 65 after the second predetermined period ΔTb elapses from the stop of the driving of the drive shaft driving source 66 after the rotation stop signal is input from the second switch SW-2. Accordingly, the driving of the fluid driving source 65 can be stopped with the delay of the second predetermined period ΔTb from the stop of the driving of the drive shaft driving source 66.

Further, in the medical device 10, the second switch SW-2 may output the rotation stop signal for the drive shaft driving source 66, the third switch SW-3 may output the fluid stop signal for the fluid driving source 65, and the controller 69 may stop the driving of the drive shaft driving source 66 when the rotation stop signal is input from the second switch SW-2 or the fluid stop signal is input from the third switch SW-3 during the driving of the drive shaft driving source 66 and the fluid driving source 65, and may stop the driving of the fluid driving source 65 after the second predetermined period ΔTb elapses from the stop of the driving of the drive shaft driving source 66. Accordingly, the driving of the fluid driving source 65 can be automatically stopped with the delay of the second predetermined period ΔTb from the stop of the driving of the drive shaft driving source 66.

In addition, in the medical device 10, the second switch SW-2 may output the rotation stop signal for the drive shaft driving source 66, the third switch SW-3 may output the fluid stop signal for the fluid driving source 65, and the controller 69 may not stop the driving of the fluid driving source 65 even when the fluid stop signal is input from the third switch SW-3 during the driving of the drive shaft driving source 66 and the fluid driving source 65 or until the second predetermined period ΔTb elapses from the stop of the driving of the drive shaft driving source 66, and may stop the driving of the fluid driving source 65 when the fluid stop signal is input from the third switch SW-3 after the second predetermined period ΔTb elapses from the stop of the driving of the drive shaft driving source 66 after the rotation stop signal is input from the second switch SW-2. Accordingly, the driving of the fluid driving source 65 can be stopped with the delay of the second predetermined period ΔTb or more from the stop of the driving of the drive shaft driving source 66.

In addition, in the medical device 10, the controller 69 may start to drive the drive shaft driving source 66 when the rotation start signal is input again from the second switch SW-2 before the second predetermined period ΔTb elapses from the stop of the driving of the drive shaft driving source 66 after the rotation stop signal is input from the second switch SW-2. Accordingly, in the state in which the negative pressure remains in the lumen 22, the drive shaft driving source 66 can be driven again to continue the collection of the debris.

It is noted that this disclosure is not limited to the embodiments described above, and various modifications can be made by those skilled in the art within a scope of the technical idea of this disclosure. In the above-described embodiments, the third switch SW-3 is provided on the handle portion 17, but a sensor that detects insertion of the shaft portion 20 into a living body may be provided at the distal portion of the shaft portion 20 and may be used as the third switch SW-3. Accordingly, the fluid start signal is automatically input to the controller 69 by inserting the shaft portion 20 into the living body.

In order to delay the start of the driving of the drive shaft driving source 66, the medical device 10 may use a pressure value indicating a pressure applied in the lumen 22 or in the vicinity thereof. In such a case, a flow sensor (not shown) is disposed in the vicinity of the cutting portion 40 of the drive shaft 20 or between the branch tube 53 and the injection tube 85. One or more flow sensors are disposed. The flow sensor measures a flow rate value at a constant interval and inputs the flow rate value to the controller 69. The controller 69 first starts to drive the fluid driving source 65, and starts to drive the drive shaft driving source 66 when the flow rate value measured by the flow sensor reaches a preset set value after the driving of the fluid driving source 65 is started. Alternatively, when the driving of the fluid driving source 65 is started, the controller 69 performs control so as to limit the start of the driving of the drive shaft driving source 66, and when the flow rate value measured by the flow sensor reaches the preset set value, the controller 69 releases the limit of the drive shaft driving source 66. Accordingly, when the negative pressure equal to or higher than a set value is not generated in the lumen 20, the start of the driving of the drive shaft driving source 66 can be prevented, and debris generated by the rotation of the drive shaft driving source 66 can be reliably collected. For example, the set value is 1 mm/min to 50 mm/min, and preferably 10 mm/min to 33 mm/min at which the thrombus can be aspirated.

In addition, the medical device 10 can also prevent clogging of the lumen 20 by using a pressure sensor (not shown). The pressure sensor is disposed in the vicinity of the cutting portion 40 of the drive shaft 20 or between the branch tube 53 and the injection tube 85. One or more pressure sensors are disposed. The pressure sensor measures the pressure applied in the lumen 20 at a constant interval, and inputs the pressure value to the controller 69. When the pressure value reaches a preset set value, the controller 69 performs input to the fluid driving source 65 such that an aspiration amount is larger than the current aspiration amount or the pressure value is changed to a preset second set value.

What is claimed is:

1. A medical device for removing an object in a body cavity, comprising:
- a rotatable drive shaft having a lumen;
- a cutter disposed at a distal portion of the drive shaft and by which the object is cut;
- a drive shaft driving source configured to rotate the drive shaft;
- a fluid driving source configured to move a fluid from a distal side to a proximal side of the lumen;
- a first sensor configured to measure a flow rate of the fluid in the lumen;
- a switch; and
- a controller configured to:
  - in response to the switch being turned on, control the fluid driving source to begin moving the fluid, and
  - control the drive shaft driving source to begin rotating the drive shaft at least a first predetermined amount of time after the switch is turned on and after the flow rate measured by the first sensor has reached a set value.

2. The medical device according to claim 1, wherein the controller is further configured to, in response to the switch being turned off, control the drive shaft driving source to stop rotating the drive shaft, and then control the fluid driving source to stop moving the fluid a second predetermined amount of time after the switch is turned off.

3. The medical device according to claim 2, wherein the second predetermined amount of time is longer than the first predetermined amount of time.

4. The medical device according to claim 1, further comprising:

a handle connectable to a proximal portion of the drive shaft and on which the switch is disposed.

5. The medical device according to claim 4, wherein the drive shaft driving source and the fluid driving source are disposed inside the handle.

6. The medical device according to claim 1, further comprising:

a second sensor configured to measure a pressure applied in the lumen, wherein the controller is further configured to control an output of the fluid driving source based on the measured pressure.

7. The medical device according to claim 1, wherein the switch is a manual switch.

8. A medical device for removing an object in a body cavity, comprising:

a rotatable drive shaft having a lumen;

a cutter disposed at a distal portion of the drive shaft and by which the object is cut;

a drive shaft driving source configured to rotate the drive shaft;

a fluid driving source configured to move a fluid from a distal side to a proximal side of the lumen;

a first switch for turning on and off the drive shaft driving source;

a second switch for turning on and off the fluid driving source; and a controller configured to control the drive shaft driving source to begin rotating the drive shaft a first predetermined amount of time after the second switch is turned on even when the first switch is turned on first.

9. The medical device according to claim 8, wherein the controller is further configured to, after the rotation of the drive shaft and the moving of the fluid are begun, control the fluid driving source to continue to move the fluid even when the second switch is turned off until the first switch is turned off and a second predetermined amount of time elapses thereafter.

10. The medical device according to claim 9, wherein the second predetermined amount of time is longer than the first predetermined amount of time.

11. The medical device according to claim 8, further comprising:

a handle connectable to a proximal portion of the drive shaft and on which the switch is disposed.

12. The medical device according to claim 11, wherein the drive shaft driving source and the fluid driving source are disposed inside the handle.

13. The medical device according to claim 8, further comprising:

a sensor configured to measure a pressure applied in the lumen, wherein the controller is further configured to control an output of the fluid driving source based on the measured pressure.

14. A method performed by a medical device for removing an object in a body cavity, the medical device including:

a rotatable drive shaft having a lumen, a cutter disposed at a distal portion of the drive shaft and by which the object is cut, a drive shaft driving source configured to rotate the drive shaft, a fluid driving source configured to move a fluid from a distal side to a proximal side of the lumen, and a switch, the method comprising:

in response to the switch being turned on, controlling the fluid driving source to begin moving the fluid, measuring a flow rate of the fluid in the lumen, and controlling the drive shaft driving source to begin rotating the drive shaft at least a first predetermined amount of time after the switch is turned on and after the measured flow rate has reached a set value.

15. The method according to claim 14, further comprising:

in response to the switch being turned off, controlling the drive shaft driving source to stop rotating the drive shaft, and then controlling the fluid driving source to stop moving the fluid a second predetermined amount of time after the switch is turned off.

16. The method according to claim 15, wherein the second predetermined amount of time is longer than the first predetermined amount of time.

17. The method according to claim 14, wherein the medical device further includes a handle connectable to a proximal portion of the drive shaft and on which the switch is disposed.

18. The method according to claim 17, wherein the drive shaft driving source and the fluid driving source are disposed inside the handle.

* * * * *